US009370479B2

(12) United States Patent
Moya Argilagos et al.

(10) Patent No.: US 9,370,479 B2
(45) Date of Patent: Jun. 21, 2016

(54) MOUTHRINSE COMPOSITION

(75) Inventors: Dally Moya Argilagos, Zurich (CH); Cornelia Scheffel, Aesch (CH); Turan Matur, Bottmingen (CH); Andre Brunella, Dornach (CH)

(73) Assignee: GABA International Holding AG (CH)

( * ) Notice: Subject to any disclaimer, the term of this patent is extended or adjusted under 35 U.S.C. 154(b) by 100 days.

(21) Appl. No.: 13/985,568

(22) PCT Filed: Feb. 18, 2011

(86) PCT No.: PCT/EP2011/052474
§ 371 (c)(1),
(2), (4) Date: Aug. 14, 2013

(87) PCT Pub. No.: WO2012/110107
PCT Pub. Date: Aug. 23, 2012

(65) Prior Publication Data
US 2013/0319883 A1 Dec. 5, 2013

(51) Int. Cl.
*A61K 8/73* (2006.01)
*A61K 8/21* (2006.01)
*A61Q 11/00* (2006.01)
*A61K 8/19* (2006.01)

(52) U.S. Cl.
CPC . *A61K 8/736* (2013.01); *A61K 8/19* (2013.01); *A61K 8/21* (2013.01); *A61Q 11/00* (2013.01)

(58) Field of Classification Search
USPC .................................................. 424/49, 401
See application file for complete search history.

(56) References Cited

U.S. PATENT DOCUMENTS

| 4,512,968 | A | 4/1985 | Komiyama et al. |
| 5,004,597 | A | 4/1991 | Majeti et al. |
| 6,638,918 | B2 | 10/2003 | Davidson et al. |
| 2010/0015068 | A1 | 1/2010 | Karp et al. |

FOREIGN PATENT DOCUMENTS

| CN | 1969801 | 5/2007 |
| GB | 2132889 | 7/1984 |
| GB | 2132889 | 7/1994 |
| JP | S56-045408 | 4/1981 |
| JP | S59-152312 | 8/1984 |
| JP | H06-084309 | 9/1987 |
| JP | H05-000930 | 1/1993 |
| JP | H08-026952 | 1/1996 |
| JP | H09-249541 | 9/1997 |
| JP | 2006-241122 A | 9/2006 |
| RU | 2113842 | 6/1998 |
| RU | 2328267 | 7/2008 |
| WO | WO 02/17868 | 3/2002 |
| WO | WO 02/074274 | 9/2002 |
| WO | WO 03/042251 | 5/2003 |
| WO | WO 2004/045446 | 6/2004 |
| WO | WO 2006/005211 | 1/2006 |
| WO | WO 2008/121518 | 10/2008 |
| WO | WO 2009/130319 | 10/2009 |
| WO | WO 2012/087327 | 6/2012 |

OTHER PUBLICATIONS

Sano et al., 2003, "Effect of chitosan rinsing on reduction of dental plaque formation," Bull. Tokyo Dent. Coll. 44(1):9-16.
Beecham Group PLC, 2007, "Medicines and Healthcare products," Regulatory Agency, http://www.mhra.gov.uk/home/groups/lunit1/documents/websiteresources/con2033849.pdf.
Schlueter et al., 2009, "Tin-containing fluoride solutions as anti-erosive agents in enamel: an in vitro tin-uptake, tissue-loss, and scanning electron micrograph study," European J. Oral Sci. 117(4):427-434.
Ganss et al., 2010, "Efficacy of a Tin/Fluoride Rinse: a Randomized in situ Trial on Erosion," J. Dental Research 89(11):1214-1218.
Schlueter et al., 2010, "Tin and fluoride as anti-erosive agents in enamel and dentine in vitro," Acta Odontologica Scandinavia 68(3):180-184.
Arnaud et al., 2010, "Chitosan Effect on Dental Enamel De-Remineralization: An in vivo Evaluation," J. Dentistry 38(11):848-852.
Chitodent, 2004, "Chitodent—the Homeopathically Compliant, Fluoride-Free Toothpaste with Chitosan," Product Information from website www.chitodent.de.
Database GNPD Mintel, 2010, "Moutwash," AN: 1405361.
Ganss et al., 2010, "Erosionen der Zahnhartsubstanzen—Pravention and Therapie, [Erosions of the Hard Tooth Substances—Prevention and Therapy]" Quintessenz 61:1203-1210.
International Search Report and Written Opinion in International Application No. PCT/EP2011/052474, mailed Jan. 24, 2012.
Written Opinion in International Application No. PCT/EP2011/052474, mailed Feb. 27, 2013.

*Primary Examiner* — Walter Webb

(57) ABSTRACT

A mouthrinse containing chitosan or pharmaceutically acceptable acid addition salt thereof with fluoride ions, for use against erosive tooth demineralization, and kits containing chitosan or pharmaceutically acceptable acid addition salt thereof with fluoride ions, wherein one of the two active agents is comprised in a mouthrinse, are described. The mouthrinse may furthermore comprise dissolved tin, in particular stannous ions. Mouthrinses containing chitosan or pharmaceutically acceptable acid addition salt thereof with fluoride ions are tested in the treatment or prevention of erosive tooth demineralization caused by citric acid.

8 Claims, No Drawings

MOUTHRINSE COMPOSITION

FIELD OF THE INVENTION

The present invention relates to the use of mouthrinses in treating or preventing erosive tooth demineralization in acidic media, brought about by food acids or endogenous acids such as gastric juice.

BACKGROUND OF THE INVENTION

There are three major sources for acids, which can cause tooth demineralization. The first source is the acids generated by cariogenic oral bacteria from food debris. These acids are carboxylic acids derived from the carbohydrates of the food debris that are metabolized by the oral bacteria. Such acids are rather weak, but act for extended periods on the teeth. The second source is the exogenous food acids that are present in the foodstuffs themselves, in particular in fruits, fruit juices or in artificial soft drinks, or in salad dressings. The third source are endogenous acids, in particular hydrochloric acid-containing gastric juice, which may come into contact with the teeth upon vomiting, such as in bulimia patients, or in reflux disease patients. These latter two types of acids are rather strong but act only for short times on the teeth. Tooth demineralisation caused by the latter two types of acids is termed "erosive tooth demineralisation" and is not related to cariogenic oral bacteria. Since acid-containing soft drinks have enjoyed a rising popularity among consumers in the past time the problem of erosive tooth demineralisation by food acids has become more acute, and a marked percentage of the overall population is nowadays afflicted by it. Similarly, a rising number of (mainly female) patients are subject to bulimia. Erosive tooth demineralisation is not noticed by the afflicted subject for quite a long time, and the pathological condition is thus often only diagnosed at a very late stage. Since erosive tooth demineralisation is considered irreversible (in contrast to tooth demineralization caused by cariogenic bacteria) it is essential that it be prevented from happening in the first place, or if it has already taken place, that it be prevented from proceeding further or that its progression be slowed down.

Fluorides are customarily used in oral care products such as toothpastes, dental gels or mouthrinses. It has been known for a long time that fluoride ion, optionally in combination with stannous ions, such as in the form of stannous fluoride, is beneficial in preventing erosive tooth demineralisation.

Chitosan has occasionally been used or studied in oral care. GB 2132889A describes oral care products containing chitin derivatives such as chitosan, and discloses that chitin or chitosan may act as a cure or prophylaxis in case of dental caries, periodontoclasia and halitosis, and that in a dentifrice chitosan salts may mask the taste of a silica abrasive. WO 02/17868A describes oral and dental hygiene agents containing chitosan microcapsules, the microcapsules being loaded with an active agent which may be, among others, stannous fluoride. Its compositions are said to have protective effect against caries, periodontosis and plaque, and to have anti-inflammatory effect. WO 03/042251A discloses compositions, such as oral care compositions, comprising chitosan in the form of nano-sized fibres and which also may contain a fluoride source. These compositions are said to improve general gum and teeth health, to be suitable for treatment of halitosis and gingivitis, to reduce staining of the teeth, to provide anti-caries, anti-plaque and anti-calculus benefits, to inhibit cariogenic bacteria, and to inhibit hydrogen sulphide and volatile odiferous organosulphide compounds produced by salivary microorganisms. For the chitosan itself it is stated that it has film-forming and pH-buffering capabilities. JP 2006/241122A discloses compositions, which may be oral care compositions, which comprise glucosamine and/or chitosan oligosaccharide, and a remineralisation promotion constituent containing a fluorine ion source. The "remineralisation" is in the case of carious lesions produced by *streptococcus mutans*. WO 2008/121518A discloses polymeric microcapsules, which may preferably be chitosan microcapsules, and which may be used in dentifrices which may contain a fluoride source. The capsules also contain a quaternary ammonium salt. The compositions are said to be antimicrobial. Recently a toothpaste called "Chitodent" has appeared on the German market. According to its advertisement it contains chitin, chitosan and silver ions, but is devoid of fluoride. Stamford Arnaud T M et al. J Dent 38 (2010)848-852 studied the remineralising effect of chitosan in human tooth samples which had been demineralized with acetate buffers of pH 4.0 and 4.8, which is a model for caries-related demineralization. Ganss C, Schlüter S. Quintessenz 61 (2010)1203-1210 discusses prospective new agents for the indication of erosive tooth demineralisation and mentions chitosan but states that "proof of activity so far is not available". In a poster by Neutard et al. presented at the 57th congress of the European Organization for Caries Research (ORCA, Montpellier, France, July 2010), activities of some fluoride-containing toothpastes and some "special free fluoride-free toothpastes" (among which was the above mentioned Chitodent) in the prevention of erosive tooth demineralisation were determined. The authors concluded that "the fluoride-free preparations had no significant effect" and that "the special formulations were not superior or even less effective compared to conventional products".

The present application seeks to provide new prevention routes against erosive tooth demineralisation caused by strong food acids or strong endogenous acids such as gastric juice.

BRIEF SUMMARY OF THE INVENTION

The task set is solved by a mouthrinse comprising dissolved chitosan or a pharmaceutically acceptable acid addition salt thereof and dissolved fluoride ions, for use against erosive tooth demineralization.

Further objects of the invention are:

A kit comprising:
a) A mouthrinse comprising dissolved chitosan or a pharmaceutically acceptable acid addition salt thereof and dissolved fluoride ions; and
b1) a container containing the mouthrinse and bearing human-readable indications disclosing that the mouthrinse is for use against erosive tooth demineralization, or
b2) a package containing a container, the container comprising the mouthrinse, and the package bearing human-readable indications disclosing that the mouthrinse is for use against erosive tooth demineralization, or
b3) a package containing a container and a leaflet, the container comprising the mouthrinse, and the leaflet bearing human-readable indications disclosing that the mouthrinse is for use against erosive tooth demineralization.

A method for the prevention of erosive tooth demineralisation or for the treatment of teeth affected by erosive tooth demineralisation in a subject in need of such prevention or treatment, comprising bringing the subject's teeth in contact with a mouthrinse comprising dissolved chitosan or a pharmaceutically acceptable acid addition salt thereof and dissolved fluoride ions.

Oral care articles containing fluoride ions as an agent against erosive tooth demineralization, and chitosan or a pharmaceutically acceptable acid addition salt thereof, as a combination for the simultaneous, separate or successive administration in the prevention or treatment of erosive tooth demineralisation, with the provisos that the oral care articles contain a mouthrinse and that either the fluoride ions or the chitosan or pharmaceutically acceptable acid addition salt thereof are dissolved in the mouthrinse.

A mouthrinse comprising 200 to 2000 ppm, preferably 250 to 1000 ppm dissolved fluoride ions, 0.05 to 5% of dissolved chitosan or a pharmaceutically acceptable acid addition salt thereof, 150 to 1000 ppm dissolved tin, 5 to 20% of glycerol and 0.3 to 5% of gluconate, all based on the mouthrinse.

Preferred embodiments of all these objects are as in the respective dependent claims and as outline hereinafter.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

DETAILED DESCRIPTION OF THE INVENTION

The following description of the preferred embodiment(s) is merely exemplary in nature and is in no way intended to limit the invention, its application, or uses.

The invention requires, as a first essential component, chitosan or a pharmaceutically acceptable acid addition salt thereof. The chitosan may be derived from chitin originating e.g. from the shells of marine crustaceans (e.g. crab, shrimp, prawn, krill, lobster, crayfish, barnacle, copepod), from insects or from fungi. The chitosan may preferably have a degree of deacetylation (DDA) of 50% to 99%, more preferably of 70% to 95% and even more preferably of 75% to 90%. The DDA (in percent) of a chitosan sample may be obtained by titration as described in example 9. The chitosan is preferably in a form where its deacetylated amino groups are protonated with a pharmaceutically acceptable acid, to form a pharmaceutically acceptable acid addition salt of the chitosan. The protonation degree, i.e. the mole fraction of deacetylated amino groups that are protonated, is preferably in the range of 80 mole % to 99 mole %, more preferably in the range of 90 mole % to 95 mole %. As pharmaceutically acceptable acids that can be used to form the pharmaceutically acceptable acid addition salt thereof may be mentioned mineral hydrohalic acids, such as hydrochloric or hydrofluoric acids; mineral oxo acids, such as sulfuric, phosphoric, or nitric acids; or organic carboxylic acids. The chitosan or pharmaceutically acceptable acid addition salt thereof preferably has an average molecular weight in the range of 5000 to 1000000 Daltons, more preferably in the range of 5000 to 500000 Daltons, particularly preferably in the range of 100000 to 400000 Daltons. This average molecular weight and molecular weight distribution may be determined in a known manner by gel permeation chromatography using e.g. N-acetyl-D-glucosamine oligomer and pullulan retention time standards, or by using a multi angle laser light scattering (MALLS) detector.

Preferably, the chitosan is not further chemically modified by additional functional groups such as hydrophilic or charged side groups, N-carboxymethyl, N,N-dicarboxymethyl, N-methylene phosphonic, N-methyl, N-monocarboxybutyl, N,N-dicarboxybutyl, 5-methylpyrrolidinone and N-trimethyl This is referred as an unmodified chitosan.

The invention requires, as a second essential component, fluoride ions. The fluoride ions may be used in the form of any fluoride ion source customarily employed in oral care compositions, such as stannous fluoride, sodium fluoride, amine fluoride or hydrofluoric acid.

The chitosan or a pharmaceutically acceptable acid addition salt thereof and the fluoride ions may either be dissolved in a single mouthrinse, containing them as a "fixed" combination. They may on the other hand be included into separate oral care formulations, wherein one formulation contains the chitosan and/or pharmaceutically acceptable salt thereof and the other oral care formulation contains the fluoride, provided that at least one of the two agents is included into a mouthrinse. Such oral care formulation kits, also designated in the following as "oral care articles" or, for short, "articles", may be intended for either simultaneous administration, i.e. the two formulations are used by one and the same subject at the same time, or for separate administration, i.e. the two formulations are used independently by one and the same subject, but not according to a specified dosage regime, or for successive administration, i.e. the two formulations are used by one and the same subject one after the other, in particular one immediately after the other, in particular according to a specified dosage regime.

An example for such an article is a kit containing, as a first oral care formulation, a mouthrinse consisting of a liquid, in particular aqueous phase and comprising dissolved chitosan or pharmaceutically acceptable acid addition salt thereof; and containing, as a second formulation, a toothpaste comprising fluoride ions dissolved in a liquid, preferably aqueous phase. In this exemplary kit, it may also be possible to include the fluoride into the mouthrinse and the chitosan or pharmaceutically acid addition salt thereof into the toothpaste, by dissolving in its liquid phase. In either of these two variants, optionally and preferably dissolved tin as described hereinbefore may be present, the tin also being preferably dissolved in the mouthrinse or the liquid phase of the toothpaste. In these mouthrinse/toothpaste kits, the toothpaste formulation may preferably contain one or more abrasives. These abrasives may be inorganic abrasives, such as precipitated silicas, aluminas, insoluble carbonates (e.g. calcium carbonate, calcium phosphate, calcium pyrophosphate), zeolites or stannous pyrophosphate; or organic abrasives such as polyethylene, polyvinyl chloride, polystyrene, polycarbonate, copolymers from (meth)acrylates and other olefinic monomers, polyamides, urea-formaldehyde resins, melamine-formaldehyde resins, phenol-formaldehyde resins, cured, pulverised epoxy resins or polyesters. A mixture of these abrasives may also be used. The skilled person in the art is well aware on how to choose the type(s) and amount(s) of abrasive(s). Toothpastes suitable for the uses of the invention may also comprise essentially non-abrasive silicas, having only a thickening effect on the toothpaste formulations.

Said articles are preferably intended for separate or sequential use of its two formulations, according to a dosage regime similar to conventional such toothpaste/mouthrinse articles.

The content of dissolved chitosan and/or its pharmaceutically acceptable acid addition salt in the mouthrinse (when it is a mouthrinse containing both active agents as a "fixed" combination) or in the oral care formulation containing the chitosan or salt thereof (in the case of articles having two or more oral care formulations) is firstly chosen at least sufficiently high such as to observe a statistically significantly higher activity, in combination with the fluoride ions, than is observed in the same experimental setup, but with fluoride ions alone. As "statistically significant" is understood if a two-sided Student's T-test, with a confidence limit of 5%, detects such significant difference in activity between the combination fluoride ions plus chitosan or salt thereof, and fluoride ions alone. Such statistically significant difference is indicative of a synergistic action between fluoride ions and the chitosan or salt thereof. The content of dissolved chitosan and/or its pharmaceutically acceptable acid addition salt is secondly chosen not higher than as to impart the mouthrinse a dynamic viscosity of at the most 1000 mPa·s. If the chitosan or pharmaceutically acceptable acid addition salt is to be included into the liquid phase of another oral care formulation, such as a toothpaste (in the case of articles having two or more oral care formulations), then that amount should preferably such as to impart the overall toothpaste a dynamic viscosity of at the most 1500 Pa·s. The skilled person is well aware on how to choose the proper amount, molecular weight and DDA of the chitosan or pharmaceutically acceptable acid addition salt thereof, in order to achieve, depending on the pH, the ionic strength and any other viscosity-affecting components of the mouthrinse or toothpaste, the desired dynamic viscosity thereof. Typically the amount of chitosan or pharmaceutically acceptable acid addition salt thereof is preferably 0.01 to 5%, more preferably 0.05 to 1%, still more preferably 0.1 to 0.7%, based on the mouthrinse, or based on the formulation in question.

The fluoride ion content of the mouthrinse (when it is a mouthrinse containing both active agents as a "fixed" combination) or in the oral care formulation containing fluoride (in the case of articles having two or more oral care formulations) is preferably from 200 to 2000 ppm, based on the mouthrinse, or based on the formulation in question. If in a mouthrinse/toothpaste kit the fluoride ions are comprised in the toothpaste, then the fluoride ion concentration of the toothpaste is more preferably from 1000 to 1600 ppm, based on the toothpaste. The fluoride ion content may be determined potentiometrically using a fluoride-selective electrode (see example 5).

The fluoride ions and the chitosan or pharmaceutically acceptable acid addition salt thereof are dissolved in the mouthrinse consisting of a liquid phase. The mouthrinse, whether containing both active agents as a "fixed" combination, or forming part of an oral care article and having only one of the two active agents, consists only of a liquid phase and is thus is a clear solution essentially, preferably completely free of suspended or sedimented solids or from turbidity. Any oral care formulations other than mouthrinses, such as toothpastes and being comprised within an oral care article, preferably comprise a liquid phase. The liquid phase is preferably at least partially aqueous. Accordingly, the liquid phase may preferably comprise about 10% to about 90%, more preferably about 25% to about 75%, based on the liquid phase, of water. A possible co-solvent for the liquid phase of the mouthrinse is ethanol, in amounts of typically 5% to 15%, based on the mouthrinse. The mouthrinse may have a pH which is physio-logically acceptable and which preferably serves to fully dissolve the entire amount of chitosan. Such pH may typically be in the range of about 3.0 to about 6.0, preferably about 4.0 to about 5.0, more preferably about 4.3 to about 4.6. If necessary the pH of the mouthrinse may be adjusted to the desired value by adding acid (such as hydrochloric acid) or base (such as sodium hydroxide).

The mouthrinse and any other oral care formulations within articles are preferably devoid of silver, meaning that they comprise preferably less than 0.05%, more preferably less than 0.001%, based on the composition, of silver.

The mouthrinse consisting of the liquid phase, or any formulation having a liquid phase and forming part of an article of the invention, furthermore preferably also comprises tin dissolved in that liquid phase. The term "dissolved tin", as used herein, is intended to encompass all ionic or non-ionic tin species in the formal oxidation states +II and/or +IV and being dissolved in the liquid phase. Examples of such dissolved tin species are hydrated stannous ions, stannous hydroxide, soluble ionic or nonionic complexes of stannous and/or stannic ions with ligands, such as with an optionally also present dissolved $C_{(3-6)}$ sugar alcohol and/or the anionic conjugate base of an optionally also present dissolved organic acid as ligands, and ionic hydroxo complexes of stannous and/or stannic ions. Preferably 60 mol % or more, more preferably 75 mol % or more of the content of dissolved tin [Sn] is tin in the formal oxidation state +II. The content of dissolved tin [Sn] of the mouthrinse (when it is a mouthrinse containing both active agents as a "fixed" combination) or in the oral care formulation containing the fluoride ions or the chitosan or pharmaceutically acceptable acid addition salt thereof (in the case of articles having two or more oral care formulations) is preferably in the range of 150 to 1000 ppm, more preferably in the range of 500 to 900 ppm. For a toothpaste contained within an article it is preferably 3000 to 4000 ppm. The total content of dissolved tin may be determined using X-ray fluorescence (see example 3). The content of dissolved tin in the formal oxidation state +II may be determined potentiometrically (see example 4). The dissolved tin may preferably be derived from a pharmaceutically acceptable stannous ion salt. Examples are stannous chloride, stannous fluoride, stannous hydroxide, stannous sulphate, with stannous chloride being preferred.

In the mouthrinses and articles intended for the uses and processes of the instant invention, the fluoride ions may be used as any fluoride salt customarily used in the field of oral care, such as stannous fluoride, sodium fluoride, sodium monofluorophosphate and amine fluoride. Preferably the fluoride is used as sodium fluoride and/or as amine fluoride, more preferably as a mixture of sodium fluoride and amine fluoride such that the amount ratio fluoride ions derived from sodium fluoride:fluoride ions derived from amine fluoride is in the range of 0.7:1 to 1.4:1, more preferably 0.9:1 to 1.1:1.

In all embodiments where amine fluoride is used the amine fluoride preferably contains ammonium cations of the formula R—NH$^+$R$_a$—[(CH$_2$)$_u$—NH$^+$R$_b$]$_v$—R$_c$, wherein R is a saturated or unsaturated straight-chain hydrocarbon residue of 10 to 20 carbon atoms, v is an integer from 0 to 1, u is an integer from 2 to 3 and R$_a$, R$_b$ and R$_c$ are independently selected from hydrogen and —CH$_2$CH$_2$OH. The residue R can have even or odd-numbered chain length, residues R having an even-numbered chain length are preferred with regard to physiological acceptability. The residues may be preferably mono-unsaturated. Examples of saturated hydrocarbon residues having an even-numbered chain length are decyl, dodecyl (lauryl), tetradecyl (myristyl), hexadecyl (cetyl, palmityl), octadecyl (stearyl) and eicosanyl. Examples of unsaturated residues having an even-numbered chain length are 9-cis-octadecen-1-yl (oleyl), 9-trans-octadecen-1-yl (elaidyl), cis,cis-9,12-octadecadien-1-yl (linolyl), cis,cis,cis-9,12,15-octadecatrien-1-yl (lino-lenyl) or 9-cis-eicosaen-1-yl (gadolyl). More preferred are $C_{18}$ alkyl or $C_{18}$ alkenyl, in particular 9-cis-octadecen-1-yl (oleyl). The most preferred cation in all embodiments of the invention is with R=oleyl, R$_a$=R$_b$=R$_c$=—CH$_2$CH$_2$OH, v=1 and u=3, i.e. wherein the amine fluoride is olaflur (N-(9-cis-octadecen-1-yl)-N,N'N'- tris(hydroxyethyl)-1,3-diaminopropane dihydrofluoride). The amount of ammonium cations may be determined according to example 6 or 7.

The mouthrinses and articles of the invention may furthermore comprise one or more $C_{(3-6)}$ sugar alcohols. The term "$C_{(3-6)}$ sugar alcohol" is intended to encompass all polyhydric alcohols with a total carbon atom number n of 3 to 6 and a molecular formula of $C_nH_{(2n+2)}O_n$. Preferably these sugar alcohols are acyclic and unbranched. Examples of the $C_{(3-5)}$ sugar alcohol are glycerol, erythritol, threitol, arabitol, xylitol, ribitol, sorbitol and mannitol. More preferred are, when the composition is a mouthrinse, glycerol in an amount of typically 5 to 20%, preferably 5 to 15%, based on the mouthrinse. The one or more $C_{(3-6)}$ sugar alcohols are dissolved in the mouthrinse or preferably dissolved in a liquid phase of one of the formulations of the article.

The mouthrinse or any other oral care formulation contained within an article may furthermore comprise an organic acid and/or salt thereof, either as part of a buffering system intended to achieve the above mentioned physiologically acceptable pH of the liquid phase, or as a complexing agent for dissolved tin species, if present. The organic acid, if present, is preferably a carboxylic acid. It is dissolved in the mouthrinse or preferably dissolved in the liquid phase of the other oral care formulation. The term "dissolved" implies here that the acid be dissolved either as the free acid or as a pharmaceutically acceptable salt of its anionic conjugate base (whichever may be the case) in the liquid phase. Preferred subgroups of organic acids are edible di- or tricarboxylic acids with 4 to 6 carbon atoms including the carboxylate carbon atoms, such as succinic, tartaric, citric, malic, fumaric and adipic acids; or edible α-hydroxy $C_{(2-6)}$carboxylic acids such as glycolic, lactic, citric, tartaric or gluconic acids. If the organic acid is dissolved in the form of a pharmaceutically acceptable salt then the counter cation may be a metal cation, such as from an alkaline metal (such as sodium or potassium), from an earth alkaline metal (such as magnesium or calcium), or from zinc. When organic acid is present, then its content is preferably in the range of 0.01 to 10%, preferably 0.05 to 5%, based on the mouthrinse or formulation in question within the article, whereby the upper limit may be given by the solubility of its conjugate base salt in the liquid phase at physiologically acceptable pH. The total content of organic acids may be determined by acidifying a known aliquot of the oral care composition to about pH 0, extracting the free organic acids with an organic solvent such as ether, and analysing the extract by calibrated GC using the silyl esters derivates of the acids. More preferably the mouthrinse or formulation within an article contains 0.3 to 1.0% of gluconic acid or of a salt thereof (i.e. gluconate).

The mouthrinses or articles of the invention may preferably also comprise chloride ions, preferably as dissolved ions in a liquid phase of the composition or of one of the formulations comprised within the article. A preferred range of the chloride content [Cl⁻] in ppm, based on the composition, is in the range $0.7[Sn] \geq [Cl^-] \geq 0.5[Sn]$. The chloride content may be determined by potentiometric titration (see example 8). The chloride may be added for example as sodium chloride, calcium chloride or stannous chloride, with the latter being preferred.

Further optional components in the mouthrinses or formulations within an article may be for instance:

Flavourings and cooling flavours, such as coumarin, vanillin, ethereal oils (such as peppermint oil, spearmint oil, aniseed oil, menthol, anethol or citrus oil) or other essences (such as apple, eucalyptus or spearmint essence). These flavourings may be present in 0% to 0.5%, preferably 0.03% to 0.3%, based on the mouthrinse or other formulation within an article.

Sweeteners, in particular artificial sweeteners such as saccharin, acesulfam, neotam, cyclamate or sucralose; natural high-intensity sweeteners such as thaumatin, stevioside or glycyrrhizin; or sugar alcohols different from the $C_{(3-5)}$ sugar alcohol, such as sorbitol, xylitol, maltitol or mannitol. These may be present in amounts of 0% to 0.2%, preferably 0.005% to 0.1%, based on the mouthrinse or other formulation within an article.

Antibacterials and/or preservatives, such as chlorhexidine, triclosan, quaternary ammonium compounds (such as benzalkonium chloride) or parabens (such as methyl or propyl paraben). The amount of antimicrobial agent is typically from 0 to about 0.5%, preferably 0.05 to 0.1%, based on the mouthrinse on other formulation within an article.

Emulsifiers or solubilisers, mainly in connection with abovementioned flavourings and/or antibacterials, which often are of low solubility in aqueous media. Examples of such emulsifiers are neutral surfactants (such as polyoxyethylene hydrogenated castor oil or fatty acids of sugars), anionic surfactants (such as sodium lauryl sulphate), cationic surfactants (such as the ammonium cations of formula (I)) or zwitterionic surfactants. These surfactants or solubilisers may be present in amounts of typically 0% to 2%, preferably 0.2% to 1.5%, based on the mouthrinse or other formulation within an article.

Thixotropic agents, such as soluble grades of hydroxypropylmethylcellulose, hydroxyethylcellulose or mucins, in an amount effective to impart the mouthrinse or other formulation within an article a thixotropic behaviour.

Stabilisers, such as polyvinylpyrrolidone.

The mouthrinses or articles are intended for use against erosive tooth demineralisation. For this purpose they are suitably provided as a kit containing the composition and human-readable indications disclosing to the subject using the composition that the composition is for use, or efficacious, against erosive tooth demineralisation. These indications may be directly printed on the container comprising the composition (such as a toothpaste tube or mouthrinse bottle), or they may be printed on a label wrapped or adhered onto the container. They may also be printed on a package, such as a cardboard box, enclosing the container. Finally they may be printed on a leaflet (a package insert), to be included into the kit.

The mouthrinses, articles or kits of the invention are for use against, and are efficacious in, the treatment or prevention, particularly the prevention of erosive tooth demineralisation caused by food acids (i.e. acids originating from foods) or by endogenous acids such as gastric juice (hydrochloric acid). As "food acids" are considered in the context of the present application such acids with a pKa value (or first pKa value, if multibasic) of 5.0 or less. Examples therefor are citric acids (e.g. from fruits), tartaric acid (e.g. from wine), oxalic acid (e.g. from rhubarb), phosphoric acid (e.g. from soft drinks), hydrated sulphur dioxide (e.g. from wine), and amino acids.

The mouthrinses, articles or kits of the invention may be used to prevent or treat erosive tooth demineralisation in a subject in need of such prevention or treatment. As "treatment" is preferably understood here the so-called "secondary prevention", which is a treatment on subjects exhibiting early or intermediate stages of erosive tooth demineralisation, in order to slow down a further progression of the demineralisation.

Patients in need of prevention are subjects having at least one of the following habits or conditions 1)-5):

1) They regularly consume acidic foods, in particular acidic beverages such as soft drinks;
2) they suffer from reflux disease or bulimia,
3) they clean their teeth to an extent to remove essentially all of the salivary pellicle on their tooth surfaces;
4) they have an anomaly in the chemical properties of their saliva, particularly such as below-normal levels of calcium and/or phosphate, or below-normal buffering capacity;
5) they exhibit insufficient saliva production (xerostomia patients).

Particularly patients in need of prevention are understood as subjects having 1) in combination with one of 3) to 5), or subjects having 2) in combination with one of 3) to 5). Patients in need of treatment, particularly in need of the abovementioned secondary prevention, are subjects having at least one of the above 1)-5), or having 1) in combination with one of 3) to 5), or having 2) in combination with one of 3) to 5); and furthermore showing the signs of early or intermediate stages of erosive tooth demineralisation.

As used throughout, ranges are used as shorthand for describing each and every value that is within the range including its boundary values. Any value within the range can be selected as the terminus of the range. In addition, all references cited herein are hereby incorporated by referenced in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

The invention will now be further explained by the following non-limiting examples. In the examples "AmF" or "AmF 297" denotes the amine hydrofluoride OLAFLUR.

Example 1

Mouthrinses Suitable for the Uses and Processes of the Invention

The mouthrinses are given in the below table 1 over their entry numbers. Mouthrinses comprising a combination of the invention are in boldface. The other ones are comparative mouthrinses.

TABLE 1

| composition | Entry 1 | Entry 2 | Entry 3 | Entry 4 | Entry 5 | Entry 6 | Entry 7 | Entry 8 Positive control (commercial meridol mouthrinse) | Entry 9 (Negative control) |
|---|---|---|---|---|---|---|---|---|---|
| fluoride ion (ppm) | 125 ppm from AmF 325 ppm from $SnF_2$ | 125 ppm from AmF 125 ppm from NaF | 125 ppm from AmF 125 ppm from NaF | 125 ppm from AmF 375 ppm from NaF | 125 ppm from AmF 125 ppm from NaF | 125 ppm from AmF 325 ppm from $SnF_2$ | 125 ppm from AmF 125 ppm from NaF | 125 ppm from AmF 125 ppm from $SnF_2$ | |
| total dissolved tin (ppm) | 1000 | 1100 | 800 | 1000 | 800 | 1000 | | | 400 |
| total fluoride ion (ppm) | 450 | 250 | 250 | 500 | 250 | 450 | 250 | | |
| AmF solution (%) | 0.893 | 0.893 | 0.893 | 0.893 | 0.893 | 0.893 | 0.893 | | |
| $SnCl_2$ (%) | | 0.216 | 0.157 | 0.196 | 0.157 | | | | |
| $SnF_2$ (%) | 0.136 | | | | | 0.136 | | | |
| NaF (%) | | 0.0276 | 0.0276 | 0.0829 | 0.0276 | | 0.0276 | | |
| sodium D-gluconate (%) | 1.000 | 1.100 | 0.750 | 1.000 | 0.750 | 1.000 | | | |
| sodium saccharin (%) | 0.075 | 0.070 | 0.070 | 0.070 | 0.070 | 0.075 | | | |
| anhydrous glycerol (%) | | 10.000 | 10.000 | 10.000 | 10.000 | | | | |
| cocamidopropyl betaine (%) | 0.200 | 0.200 | 0.200 | 0.200 | 0.200 | 0.200 | 0.150 | | |
| PEG-40 hydrogenated castor oil (%) | 0.500 | 0.500 | 0.500 | 0.500 | 0.500 | 0.500 | 0.150 | | |
| fragrance (%) | 0.130 | 0.135 | 0.135 | 0.135 | 0.135 | 0.135 | 0.080 | | |
| xylitol (%) | | | | | | 0.850 | | | |
| chitosan (%) | | | | | 0.300 | | 0.300 | | |
| PVP (%) | | | | | | 0.500 | | | |
| HCl 20% (%) | | | | | 0.250 | | 0.215 | | |
| KOH 20% (%) | | 0.100 | 0.050 | | 0.104 | | 0.075 | | |
| polyaminopropyl biguanide (%) | | | | | | | 0.050 | | |
| saccharin (%) | | | | | | | 0.050 | | |
| deionized water (%) | 97.066 | 86.7584 | 87.2174 | 86.9231 | 86.6134 | 95.711 | 98.0094 | | |

Example 2

In Vitro Demineralisation Tests with Mouthrinses Containing a Combination of the Invention The tested oral care compositions were all those given in table 1 of example 1, i.e. 2 mouthrinses containing a combination according to the invention, 5 comparative mouthrinses, and one negative control and one positive control mouthrinse, thus 9 different test compositions.

The tests were carried out in vitro on 108 longitudinal enamel samples cut from extracted third molar teeth, these samples being distributed into 9 groups, matching the above 9 test compositions. For each test composition 12 samples were thus available. The enamel samples were prepared as follows: From the teeth were removed any remaining soft tissues and the roots. From each of the remaining teeth crown surfaces were excised four samples of about 1 mm thickness in the longitudinal direction (using an Exact cutting system, "Exact Apparatebau", Norderstedt, Germany), to yield a flat test surface of at least 3×3 mm. This test surface was polished using firstly grit paper of nominal grain size 12 µm (Leco, St. Joseph, USA), then of nominal grain size 5 µm (Leco, St. Joseph, USA). All cutting and polishing operations were carried out under sufficient water cooling. A total of 108 enamel samples was prepared in this way, and were glued onto microscopy slides using a light-curing adhesive (Technovit 7230 VLC, Kulzer-Exact, Wehrheim, Germany). Half of each test surface was covered with the light-curing adhesive, the remaining uncovered part of the test areas was carefully inspected for adhesive contamination. The samples so prepared were stored in a humid chamber at 100% relative humidity until further use.

The 9 sample groups were subjected for 10 days (2×5 working days) to a daily sequence of demineralising treatments using 0.05 M citric acid and of treatments with one of the 9 test compositions. For this, the microscopy slides carrying the enamel samples were inserted into supports (colouring racks, Schott, Mainz, Germany) which allowed easy submersion of the microscopy slides carrying the enamel samples into the treatment and demineralisation solutions. The daily sequence consisted in a first erosive demineralisation treatment of 5 minutes, then one treatment with the test composition in question for 2 minutes, then a further five demineralisation treatments under the same conditions as in the first demineralisation treatment, and finally a last treatment with the test composition in question, under the same conditions as in the first treatment with the test composition in question. After each treatment (erosive or with the test solutions) the samples were rinsed with water for 1 min. When not treated with the erosive solution or the test composition in question the samples were stored, inserted into the said supports, in the said aqueous remineralisation solution containing 0.4 g $H_3PO_4$, 1.5 g KCl, 1 g $NaHCO_3$, and 0.2 g $CaCl_2$ per liter of solution.

After the said 10 day test period the protective coating was removed from the protected halves of the test areas and the resulting loss of enamel mineral on the unprotected halves of the test areas was determined by profilometry. The profilometric determination of the demineralisation extent was a measurement of height difference between reference part and test part of the sample surface, determining the height profile over the vertical and horizontal movements of the probe (D-profile). The measuring length was 0.75 mm. The height profiles of the enamel samples were measured with a Perthometer S8P (Perthen Mahr, Goettingen, Germany) with an optical probe (Rodenstock, Munich, Germany). The object slides with the enamel samples glued onto them were fixed onto the xy-table of the profilometer with a mouldable fixing mass. For each of the samples three profilometric traces were performed. The profilometric traces were evaluated using a special software (Perthometer Concept 4.0, Perthen Mahr, Goettingen, Germany). With this software two height lines were determined by linear regression. The first was from the height profile found on the reference area of the sample, allowing the alignment of the profile in an x-y coordinate axis system. The second linear regression height was determined from the height profile of the test area of the sample. For both linear regression determinations a section at less than 0.2 mm distance from the border line of the reference (or test) area was disregarded. The height difference between the centre points of the two linear regression lines in micrometers, averaged from the three runs for each sample, was considered as the extent of demineralisation of that sample.

The obtained data were checked for sufficient normal distribution (Kolmogorov-Smirnov test). The comparison of the results of all probands for each of the tested solution was done by simple variation analysis (ANOVA) with the posthoc test according to Tukey. The obtained results (mean and standard deviation SD from the 12 samples for each test composition) were according to the following table 2:

TABLE 2

| Entry of table 1 of example 1 | enamel loss [micrometres] | |
|---|---|---|
| | mean | SD |
| 1 | 47.0 | 8.6 |
| 2 | 48.7 | 10.3 |
| 3 | 47.8 | 9.8 |
| 4 | 50.7 | 11.1 |
| 5 | 41.3 | 8.6 |
| 6 | 47.6 | 8.5 |
| 7 | 89.4 | 8.8 |
| 8 | 56.3 | 10.9 |
| 9 | 116.2 | 5.6 |

It can be seen from table 2 that adding a combination of chitosan/chitosan salt with fluoride to a mouthrinse (entry 7) gives a mouthrinse which is more active than the negative control (entry 9), i.e. it has lower enamel loss. This is in contrast to the prior art, which did not see any effect when using chitosan alone (see the discussion of the prior art at the beginning). When furthermore dissolved tin, e.g. in the form of stannous fluoride and/or stannous chloride, is added (entry 5), then the efficacy of such mouthrinse is statistically significantly better than the other comparative mouthrinses. It appears that using chitosan and fluoride in combination gives a more reproducible effect of the mouthrinse, as can be derived from the very narrow distribution observed in entry 7; this reproducibility is also largely maintained in the case of a mouthrinse having the ternary combination chitosan or pharmaceutically acceptable salt thereof+fluoride+dissolved tin (entry 5). Table 2 also shows that adding chitosan to a mouthrinse already containing a combination of fluoride ions and dissolved tin increases the efficacy of such modified mouthrinse (entry 3 vs. entry 5), which is again contrary to what the prior art observed for chitosan alone. Table 2 furthermore shows that adding some chitosan or pharmaceutically acceptable salt thereof, at a given content of dissolved tin, gives a more pronounced increase in efficacy than further increasing the amount of dissolved tin (entries 1, 6, 2 and 4 vs. entry 5). Table 2 also shows that adding the known film former PVP (instead of chitosan) to a mouthrinse containing a combination of stannous ion and fluoride does not produce an increase in efficacy (entry 1 vs. entry 6). This indicates that the mechanism of action of chitosan or of the pharmaceutically acceptable acid addition salt thereof is not, or not only, by way of film formation on the surface of the teeth.

Example 3

Determination of the Total Content of Dissolved Tin [Sn] by X-Ray Fluorescence in an Oral Care Composition As the x-ray fluorescence spectrometer a Thermo Noran QuanX is used. Two solutions are measured:

Solution 1: 5 g of the oral care composition is directly filled into a XRF-cup. The XRF-cup is then closed with a polyethylene foil with the appropriate closing ring and is followingly inserted into the autosampler of the instrument.

Solution 2 is as solution 1, but with a known amount of furthermore added stannous salt [ΔSn] in the range of 80% to 120% of the expected ppm value of [Sn] of the sample solution.

Solutions 1 and 2 are each irradiated for 600 seconds with x-ray at 50 kV excitation, using a copper filter, $K_\alpha$-line at 25.193 keV. The integrated area under the fluorescence intensity peak of solution 1 is taken as $A_1$ and the integrated area under the fluorescence intensity peak of solution 2 is taken as $A_2$.

The dissolved tin content in ppm based on the composition, [Sn], is obtained as $$[Sn] = [\Delta Sn]\frac{A_2}{A_2 - A_1}$$

Example 4

Measurement of Dissolved Tin at Formal Oxidation State +II in an Oral Care Composition A combined platinum electrode type 6.1204.310 of Metrohm, Switzerland, and a potentiometer Titrando 809 of Metrohm, Switzerland, are used. The calibration of the electrode is done according to the manual.

10.0000 g of the oral care composition are exactly weighed (±0.1 mg) in a 100 ml container and 40 ml water, 5 ml 32% HCl and a known aliquot v (in ml) of standard 0.05 M $KI_3$ solution is added, such that iodine is added in excess of the tin in formal oxidation state +II contained in the sample (a typical value for v is 5 ml).

The electrode is immersed into the sample solution and the remaining iodine not already reduced to $I^-$ by the tin in formal oxidation state +II is titrated back with standard 0.1 M $Na_2S_2O_3$ solution to the endpoint of the titration. The used amount of $Na_2S_2O_3$ solution in ml is taken as $v_1$.

The tin in formal oxidation state +II contained in the sample in ppm based on the oral composition, $[Sn^{+II}]$, is obtained as $$[Sn^{+II}] = 593.45(v-v_1)$$

Example 5

Potentiometric Fluoride Determination in an Oral Care Composition

A fluoride-selective electrode type 6.0502.150 of Metrohm, Switzerland, a pH/Ion-meter 692, Metrohm, Switzerland and an Ag/AgCl reference electrode type 6.0750.100, Metrohm, Switzerland are used.

A total ionic strength adjusted buffer (TISAB) is required and made as follows: A solution of 160 mg NaOH in 2 liters of water is prepared (solution 1); 25 g 1,2-diaminocyclohexane-N,N,N',N'-tetraacetic acid, 290 g NaCl and 285 ml glacial acetic acid are dissolved in 2 liters of water (solution 2); then solutions 1 and 2 are mixed and filled up to 5 liters with water.

The calibration of the fluoride-selective electrode is performed according to the manual of the pH/Ion-meter.

1.0000 g±0.1 mg of the oral care composition are exactly weighed in a 50 ml plastic container and filled up with water to a weight of 20.0000 g±0.1 mg, and 20 ml of above mentioned TISAB buffer are added. The fluoride-selective electrode and the reference electrode are immersed into the sample and the potential is read off after 5 minutes, according to the manual of the pH/Ion-meter. The fluoride concentration in ppm is calculated by multiplying the measured response-value by 40 (the total dilution factor from the oral care composition to the measured sample), and dividing by the weight of the oral care composition sample in g.

Example 6

Determination of Ammonium Cations of Formula R—$NH^+R_a$—$[(CH_2)_u$—$NH^+R_b]_v$—$R_c$ with $R_a$, $R_c$=Hydrogen and v=0, or with $R_b$, $R_c$=Hydrogen and v=1, in an Oral Care Composition The determination is done using densitometric quantification on reverse phase HPTLC plates after staining with ninhydrine.

Procedure:

Ninhydrine solution: Dissolve 2 g of ninhydrine purum in 1000 ml of ethanol p.a. The solution has to be stored in a glass bottle at 4° C. (maximal storage time: 1 month).

A reference solution of the ammonium cation to be determined is prepared by dissolving an exactly known amount of the corresponding pure amine hydrofluoride in methanol p.a., to make a solution containing an exactly known content of the amine fluoride in the range of about 3000 ppm, based on the solution. This reference solution is designated in the following as R.

Sample solution: Accurately weigh (to within 0.1 mg) an amount M of approximately 1 g of the oral care composition in a 25 ml measuring flask and make up to volume with methanol p.a. Expose to ultrasonic radiation for about 20 minutes. This solution is designated as S.

The HPTLC plate is Silicagel 60 without fluorescence indicator, 10×20 cm (Merck no. 5626).

The reference solution and the sample solution are applied onto the HPTLC plate using an applicator Linomat IV (Camag, Switzerland) according to the following track scheme:

| Track No. | Solution | Amount applied (μl) |
|---|---|---|
| 1 | R | 2 |
| 2 | S | 10 |
| 3 | R | 4 |
| 4 | S | 10 |
| 5 | R | 6 |
| 6 | S | 10 |
| 7 | R | 8 |
| 8 | S | 10 |
| 9 | R | 10 |
| 10 | S | 10 |

-continued

| Track No. | Solution | Amount applied (μl) |
|---|---|---|
| 11 | R | 2 |
| 12 | S | 10 |
| 13 | R | 4 |
| 14 | S | 10 |
| 15 | R | 6 |
| 16 | S | 10 |
| 17 | R | 8 |
| 18 | S | 10 |
| 19 | R | 10 |
| 20 | S | 10 |

Each track has an initial width on the plate of 4 mm; the initial distance between two tracks is 5 mm and the initial distance from one outermost track to the adjacent edge of the plate is 11 mm.

The plate is developed with ethanol:25% aqueous ammonia 9:1 (v/v) as the eluent to a migration distance of about 6 cm (under these conditions e.g. the ammonium cation of formula (I) with $R_a$, $R_c$=hydrogen and R=9-octadecen-1-yl migrates to an $R_f$ value of about 0.6). The plate is then immersed in the ninhydrine solution for 10 min and dried for 10 min at 100° C.

Calculation:

The areas of all developed spots are evaluated densitometrically with light of wavelength 480 nm using a TLC scanner 3 (CAMAG, Switzerland).

The areas obtained from tracks 1, 3, 5, 7 and 9 are used to obtain a first parabolically approximated calibration curve of area vs. amount of amine fluoride in mg. A second such calibration curve is obtained from tracks 11, 13, 15, 17 and 19.

The average area from sample tracks 2, 6, 10, 14 and 18 is converted to an amount [am1] amine fluoride in mg using the first calibration curve. The average area from sample tracks 4, 8, 12, 16 and 20 is similarly converted to an amount [am2] amine fluoride in mg using the second calibration curve.

The content of ammonium cations of formula (I) I ppm, based on the oral care composition, [AM], is then obtained as $$[AM] = \frac{1250([am1] + [am2] + [am2])}{M} \times \frac{(MW - 19(v + 1))}{MW}$$

wherein M, [am1] and [am2] are as defined above, MW is the molecular weight of the pure amine fluoride used to prepare solution R, and v is as defined for formula (I).

Example 7

Determination of Ammonium Cations of Formula R—NH$^+$R$_a$—[(CH$_2$)$_u$—NH$^+$R$_b$]$_v$—R$_c$, Derived from Amine Fluoride in an Oral Care Composition The procedure of this example is applicable to all other ammonium cations of formula (I) not falling under the definitions given in the heading of example 6. This determination is done on reverse phase HPTLC plates after staining with Berlin Blue.

Berlin Blue solution: Dissolve 4 g of potassium hexacyanoferrate(III) p.a. in 150 ml distilled water and add 350 ml of acetone p.a. Dissolve separately 7.5 g iron(III)chloride hexahydrate p.a. in 500 ml ethanol p.a. Mix immediately prior to use 40 ml of each of the two solutions and 80 ml of ethanol p.a.

A reference solution of the ammonium cation to be determined is prepared by dissolving an exactly known amount of the corresponding pure amine hydrofluoride in methanol p.a., to make a solution containing an exactly known content of the amine fluoride in the range of about 500 ppm, based on the solution. This reference solution is designated as R.

Sample solution: Accurately weigh (to within 0.1 mg) an amount M of approximately 1 g of the oral care composition in a 100 ml measuring flask and make up to volume with methanol p.a. Expose to ultrasonic radiation for about 15 minutes. This solution is designated as S.

The HPTLC plate is Silicagel 60 without fluorescence indicator, 10×20 cm (Merck no. 5626).

The reference solution and the sample solution are applied onto the HPTLC plate using an applicator Linomat IV (Camag, Switzerland) according to the following track scheme:

| Track No. | Solution | Amount applied (μl) |
|---|---|---|
| 1 | R | 1 |
| 2 | S | 3 |
| 3 | R | 2 |
| 4 | S | 3 |
| 5 | R | 3 |
| 6 | S | 3 |
| 7 | R | 4 |
| 8 | S | 3 |
| 9 | R | 5 |
| 10 | S | 3 |
| 11 | R | 1 |
| 12 | S | 3 |
| 13 | R | 2 |
| 14 | S | 3 |
| 15 | R | 3 |
| 16 | S | 3 |
| 17 | R | 4 |
| 18 | S | 3 |
| 19 | R | 5 |
| 20 | S | 3 |

Each track has an initial width on the plate of 4 mm; the initial distance between two tracks is 5 mm and the initial distance from one outermost track to the adjacent edge of the plate is 11 mm.

The plate is developed with n-pentanol:ethanol:diethyl ether:25% aqueous ammonia 3:3:3:1 (v/v/v/v) as the eluent to a migration distance of about 6 cm (under these conditions e.g. the ammonium cation of formula (I) with $R_a$, $R_b$, $R_c$=2-hydroxyethyl, R=9-octadecen-1-yl, v=1 and u=3 migrates to an $R_f$ value of about 0.8). The plate is then immersed in the Berlin Blue solution for 10 min and dried for 10 min at 100° C.

Calculation:

The areas of all developed spots are evaluated densitometrically with light of wavelength 592 nm using a TLC scanner 3 (CAMAG, Switzerland).

The areas obtained from tracks 1, 3, 5, 7 and 9 are used to obtain a first parabolically approximated calibration curve of area vs. amount of amine fluoride in μg. A second such calibration curve is obtained from tracks 11, 13, 15, 17 and 19.

The average area from sample tracks 2, 6, 10, 14 and 18 is converted to an amount [am1] amine fluoride in μg using the first calibration curve. The average area from sample tracks 4, 8, 12, 16 and 20 is similarly converted to an amount [am2] amine fluoride in μg using the second calibration curve.

The content of ammonium cations of formula (I) I ppm, based on the oral care composition, [AM], is then obtained as $$[AM] = \frac{100000([am1] + [am2])}{6M} \times \frac{(MW - 19(v+1))}{MW}$$

wherein M, [am1] and [am2] are as defined above, MW is the molecular weight of the pure amine fluoride used to prepare solution R, and v is as defined for formula (I).

Example 8

Potentiometric Chloride Determination in an Oral Care Composition

A combined silver/silver chloride electrode type 6.0350.100 of Metrohm, Switzerland, and a potentiometer Titrando 809 of Metrohm, Switzerland, are used. The calibration of the electrode is done according to the manual.

1000±0.1 mg of the oral care composition are exactly weighed in a 100 ml plastic container and 50 ml water and 2 ml 65% nitric acid are added.

The electrode is immersed into the sample and the sample is titrated with standard 0.01 M silver nitrate solution to the endpoint of the titration. The used volume of silver nitrate solution in ml is taken as v.

The chloride contained in the sample in ppm based on the composition, [Cl$^-$], is obtained as

[Cl$^-$]=354.5v

Example 9

Determination of the Degree of Deacetylation (DDA) of a Chitosan Sample

The DDA is determined on the fully protonated chitosan sample by direct titration using NaOH as a titrant. The amount of NaOH used between the pH range of 3.75 and 8.00 gives a way to calculate the degree of deacetylation in the chitosan sample. The chitosan is used in powder form of at the most 20 mesh particle size, if necessary the chitosan is ground beforehand to obtain such particle size. 100.0 mg of such chitosan powder, corrected for dry matter content, are accurately weighted, dissolved in 25 ml of 0.06 M HCl and stirred for 1 hour at room temperature until full dissolution. The solution is then diluted to 50 ml with 25 ml deionized water. The pH of the solution is now about 1.9. This solution is titrated from a buret with standardized 0.1000 N NaOH solution under stirring using a calibrated glass pH electrode, until the solution reaches a pH of 3.75. The buret volume reading at this point (in ml) is taken as $V_1$. Titration with standardized 0.1000 N NaOH under stirring is continued until the solution has a pH of 8.00 remaining stable for 10 seconds. The buret volume reading at this point (in ml) is taken as $V_2$. The DDA is then calculated according to the formula $$DDA = \frac{16116 * (V_2 - V_1) * N}{(W_1)}$$

wherein $V_1$ is the buret volume reading at pH=3.75, $V_2$ is the buret volume reading at pH=8.00 stable for 10 seconds, N is the concentration of NaOH in moles/liter, i.e. 0.1000 moles/liter, and $W_1$ is the weighted amount of moisture corrected chitosan in milligrams, i.e. 100.0 mg.

What is claimed is:

1. A mouthrinse comprising 0.05 to 5% of dissolved chitosan or a pharmaceutically acceptable acid addition salt thereof, 200 to 2000 ppm of dissolved fluoride ions, and 150 to 1000 ppm of dissolved tin for use against erosive tooth demineralization.

2. The mouthrinse of claim 1, wherein the chitosan comprises unmodified chitosan.

3. The mouthrinse of claim 1 comprising 200 to 2000 ppm dissolved fluoride ions, 0.05 to 5% of dissolved chitosan or a pharmaceutically acceptable acid addition salt thereof, 150 to 1000 ppm dissolved tin, 5 to 20% of glycerol and 0.3 to 5% of gluconate, all % based on the mouthrinse.

4. Oral care articles containing 200 to 2000 ppm of fluoride ions as an agent against erosive tooth demineralization, 0.05 to 5% of chitosan or a pharmaceutically acceptable acid addition salt thereof, and 150 to 1000 ppm of dissolved tin, all % based on the mouthrinse, as a combination for the simultaneous, separate or successive administration in the prevention or treatment of erosive tooth demineralisation, with the provisos that the oral care articles contain a mouthrinse and that either the fluoride ions or the chitosan or pharmaceutically acceptable acid addition salt thereof are dissolved in the mouthrinse.

5. The oral care articles of claim 4, wherein the fluoride ions are dissolved in the mouthrinse.

6. The oral care articles of claim 4, wherein the chitosan or pharmaceutically acceptable acid addition salt thereof is dissolved in the mouthrinse.

7. The mouthrinse of claim 3, wherein the amount of dissolved fluoride ion is between 250 to 1000 ppm.

8. The mouthrinse of claim 7, wherein the chitosan comprises unmodified chitosan.

* * * * *